United States Patent
Lee et al.

(10) Patent No.: US 10,105,299 B2
(45) Date of Patent: Oct. 23, 2018

(54) METHOD OF USING SONOCHEMICAL ACTIVACTION TO FORM META-STABLE SUBSTANCES

(71) Applicant: THE RESEARCH FOUNDATION FOR THE STATE UNIVERSITY OF NEW YORK, Albany, NY (US)

(72) Inventors: Alexander Lee, Hauppauge, NY (US); Wilson Lee, Hauppauge, NY (US); Miriam Rafailovich, Plainview, NY (US)

(73) Assignee: THE RESEARCH FOUNDATION FOR THE STATE UNIVERSITY O F NEW YORK, Albany, NY (US)

( * ) Notice: Subject to any disclaimer, the term of this patent is extended or adjusted under 35 U.S.C. 154(b) by 0 days.

(21) Appl. No.: 15/301,973

(22) PCT Filed: Apr. 10, 2015

(86) PCT No.: PCT/US2015/025393
§ 371 (c)(1),
(2) Date: Oct. 5, 2016

(87) PCT Pub. No.: WO2015/157685
PCT Pub. Date: Oct. 15, 2015

(65) Prior Publication Data
US 2017/0172874 A1    Jun. 22, 2017

Related U.S. Application Data

(60) Provisional application No. 61/977,887, filed on Apr. 10, 2014.

(51) Int. Cl.
*B05D 7/00*     (2006.01)
*A61K 8/27*     (2006.01)
(Continued)

(52) U.S. Cl.
CPC .............. *A61K 8/27* (2013.01); *A61K 8/0241* (2013.01); *A61K 8/29* (2013.01); *A61K 8/416* (2013.01);
(Continued)

(58) Field of Classification Search
CPC ........................................................ A61K 8/27
(Continued)

(56) References Cited

U.S. PATENT DOCUMENTS 5,525,440 A * 6/1996 Kay .................. H01G 9/20
                                                        205/162
5,736,128 A * 4/1998 Chaudhuri ........... A61K 8/8147
                                                        424/78.02
(Continued)

FOREIGN PATENT DOCUMENTS

| WO | 2010019413 A2 | | 2/2010 |
| WO | WO 2014011456 | * | 7/2013 |
| WO | 2014011456 A1 | | 1/2014 |

*Primary Examiner* — Tabatha L Penny
(74) *Attorney, Agent, or Firm* — Hoffmann and Baron, LLP (57) ABSTRACT

A method for forming a coated particle having a core particle that is fully coated by a dual-layer coating that includes an inner layer formed of a hydrophilic composition and an outer layer formed of a hydrophobic polymer. The core particles are added to a hydrophilic solution and mixed together. The hydrophobic polymer is then added to form a mixture. The mixture is sonicated to coat the particles and the coated particles are separated and dried to form meta-stable coated particles.

20 Claims, 5 Drawing Sheets

(51) Int. Cl.

| | | |
|---|---|---|
| *A61K 8/29* | (2006.01) | |
| *A61K 8/41* | (2006.01) | |
| *A61Q 1/00* | (2006.01) | |
| *A61Q 1/02* | (2006.01) | |
| *A61Q 17/04* | (2006.01) | |
| *A61K 8/81* | (2006.01) | |
| *A61K 8/891* | (2006.01) | |
| *A61K 8/02* | (2006.01) | |
| *A61K 8/893* | (2006.01) | |

(52) U.S. Cl.
CPC ........ *A61K 8/8129* (2013.01); *A61K 8/8152* (2013.01); *A61K 8/8164* (2013.01); *A61K 8/891* (2013.01); *A61K 8/893* (2013.01); *A61Q 1/00* (2013.01); *A61Q 1/02* (2013.01); *A61Q 17/04* (2013.01); *A61K 2800/413* (2013.01); *A61K 2800/5426* (2013.01); *A61K 2800/622* (2013.01); *A61K 2800/624* (2013.01); *A61K 2800/651* (2013.01); *A61K 2800/82* (2013.01)

(58) Field of Classification Search
USPC .......................................................... 427/212
See application file for complete search history.

(56) References Cited

U.S. PATENT DOCUMENTS

| | | | |
|---|---|---|---|
| 6,923,987 B2* | 8/2005 | Kai | .................. A61K 33/14 424/400 |
| 7,135,206 B2 | 11/2006 | Schichtel | |
| 2007/0231395 A1* | 10/2007 | Kai | .................. A61K 9/0095 424/490 |
| 2008/0031832 A1 | 2/2008 | Wakefield et al. | |
| 2011/0014298 A1* | 1/2011 | Friel | .................. A61K 8/0241 424/497 |

* cited by examiner

METHOD OF USING SONOCHEMICAL ACTIVACTION TO FORM META-STABLE SUBSTANCES

This application claims priority from international patent application No. PCT/US2015/025393, filed on Apr. 10, 2015, which claims priority from provisional application Ser. No. 61/977,887, filed on Apr. 10, 2014, both of which are incorporated herein in their entirety.

FIELD OF THE INVENTION

The present invention utilizes electrochemical activation to generate meta-stable substances mostly from water and compounds dissolved in it by way of electrochemical exposure, and as a result, generating meta-stable solutions in various technological processes instead of chemically stable reagents. This meta-stable substance will attach to the surface of a core particle as an inner layer and then followed by a hydrophobic polymer with branched moieties to wrap around the particle to prevent the meta-stable substance from reacting with its surroundings.

BACKGROUND OF THE INVENTION

Electrochemical activation processes are well known in the water treatment purification industry. As a result of electrochemical processes, both water and brine solution become meta-stable and can be further used in different physical and chemical processes. In a typical electrochemical process, an electrical power source is connected to two electrodes, or two plates (typically made from some inert metal such as platinum, stainless steel or iridium), which are placed in the water. Hydrogen will appear at the cathode (the negatively charged electrode, where electrons enter the water) and oxygen will appear at the anode (the positively charged electrode). Assuming ideal faradaic efficiency, the amount of hydrogen generated is twice the amount of oxygen, and both are proportional to the total electrical charge conducted by the solution. Water and brine solutions activated at the cathode electrode demonstrate high electron activity and anti-oxidant properties. Whereas, water and brine solutions activated at the anode electrode possess low electron activity and oxidant properties. The effect of water meta-stability is the basis for processes relating to water conditioning, purification and decontamination, as well as for the technologies of transforming water and brine solutions into environmentally friendly, anti-microbial liquids.

The use of silicone coatings on the surfaces of particles is known. For example, powder treatment with special silicones has been developed to improve the compatibility between the treated powder and a variety of oils, such as fluorinated oils or silicone oils, and also, to enhance the stability of powder and oils in emulsion systems. One such special silicone is a one-end reactive silicone-grafted silicone compound that has an extremely high water repellency, dispersibility in volatile oils, and good usability as a powder coating. The special silicone compound can be used as a powder-treating agent in any known method for powder-surface treatment.

The surface treatment of pigments has also found to make it easier to incorporate them into cosmetic formulations. For example, pigments coated with different types of silicones are commercially available and, when used as cosmetic pigments in formulations, the coating facilitates the incorporation of the pigment into hydrophobic formulations; whereas the untreated pigment would generally have little affinity. Unfortunately, silicone polymers are generally unsuitable for particle encapsulation using spraying/drying techniques.

Some pigments are coated with fluorocarbon polymers to improve their adhesive power, while also forming a film upon application. Other pigments are coated with natural polymers, such as collagen proteins. However, these types of coatings are not favorable for adhesion of the pigment to the skin and can experience manufacturing difficulties, especially in make-up formulations. The advantage of this type of coating is the ability to introduce molecules, or more specifically, macromolecules such as proteins into formulations, even though they are generally anhydrous or have low water content. It is therefore desirable to provide coated or surface-treated particles while overcoming the above-described disadvantages of conventional coatings. There is also a need to provide new materials and methods for improved particle surface treatment.

Nanomaterials are materials that have a dimension of less than 100 nm, which are similar in size to proteins in the body. Nanomaterials may occur both naturally and synthetically. They can take the form of many different shapes, such as nanotubes, nanowires, crystalline structures such as quantum dots and fullerenes. They can also be made of many different types of materials, such as carbon, silicon, gold, cadmium, selenium, and metal oxide. Nanomaterials have broad applications in many technological fields. For example, titanium dioxide or zinc oxide nanoparticles have been used in sunscreens and cosmetics for sun protection. The titanium dioxide or zinc oxide nanoparticles are transparent and do not give the cosmetics the white, chalky appearance that is typically observed with coarser bulk titanium dioxide particles. However, upon illumination by ultra-violet (UV) light, the titanium dioxide or zinc oxide nanoparticles may release free oxygen radicals (e.g., superoxide and hydroxyl radicals). These free oxygen radicals are capable of oxidizing or decomposing compounds in the surrounding environment. Therefore, when formulated into sunscreen compositions, the titanium dioxide or zinc oxide nanoparticles may adversely affect the overall stability of the sunscreen compositions. Further, the titanium dioxide and zinc oxide nanoparticles have enhanced affinity to the skin surface, in comparison with their respective larger sized counterparts, and they tend to settle into wrinkles or creases on the skin surface.

It is thus also desirable to provide coated or surface-treated nanoparticles of improved properties, in comparison with their uncoated or untreated counterparts. It is particularly desirable to provide coated or surface-treated titanium dioxide or zinc oxide nanoparticles that are suitable for use in sunscreens with little or no impact on the stability of the overall sunscreen compositions, as well as little or no tendency to settle into the wrinkles or creases on the skin surface.

SUMMARY OF THE INVENTION

In one aspect, the present invention relates to a treated particle having a core particle that is fully coated by a dual-layer coating. The dual-layer coating comprises, consists of or consists essentially of an inner layer formed of a catholyte and an outer layer formed of a hydrophobic polymer. The hydrophobic polymer in the outer layer contains branched moieties that penetrate through the inner layer so as to anchor the inner layer onto the surface of the core particle. Preferably, but not necessarily, the branched moieties of the hydrophobic polymer are covalently bound to the surface of the core particle. The inner layer may further comprise, consist of or consist essentially of a hydrophilic active agent, such as, for example, a cationic charge in the meta-stable form.

In another aspect, the present invention relates to a method for coating a core particle, the method comprising, consisting of or consisting essentially of: (a) preparing an aqueous solution of a catholyte; (b) adding the core particle to the aqueous solution; (c) adding water and a hydrophobic polymer having branched reactive ethoxy moieties to the aqueous solution; (d) sonicating the aqueous solution to form a coated particle comprising, consisting of or consisting essentially of an inner layer comprising, consisting of or consisting essentially of the catholyte and an outer layer comprising, consisting of or consisting essentially of the hydrophobic polymer with branched reactive ethoxy moieties on the surface of the core particle. Preferably, but not necessarily, the method further comprises, consists of or consists essentially of adding a hydrophilic active agent to the aqueous solution before addition of the core particle.

In a further aspect, the present invention relates to a treated particle comprising, consisting of or consisting essentially of a zinc oxide core particle coated by an inner layer comprising, consisting of or consisting essentially of an catholyte and an outer layer comprising, consisting of or consisting essentially of a silicone having: branched reactive ethoxy moieties, wherein the branched reactive ethoxy moieties of the silicone extend from the outer layer through the inner layer onto the surface of the zinc oxide core particle. Preferably, but not necessarily, the zinc oxide core particle has a particle size of less than 500 nm, more preferably less than 250 nm and most preferably less than 100 nm.

In still another aspect, the present invention relates to a topical composition comprising, consisting of or consisting essentially of the treated particle as described hereinabove and one or more skin care additives. Preferably, such skin care additives comprise, consist of or consist essentially of a component that is oxidizable by free oxygen radicals, such as, for example, organic sunscreen agents or organic dyes. Other aspects and objectives of the present invention will become more apparent from the ensuring description, examples, and claims.

DETAILED DESCRIPTION OF THE INVENTION

The surface of the core particles of the present invention is fully coated with two layers, namely an inner layer and an outer layer, to render a treated particle. The core particle useful in the present invention can be any non-agglomerated particle. The treated particle, when it is fully coated, has a density less than water (i.e., has a density less than 1). As the fully coated particle is lighter than water, it therefore, floats on water. The core particle can be a water-insoluble or water-soluble, porous or non-porous solid material that is capable of being coated by sonochemical means to permit a continuous deposition of the inner layer and the outer layer onto its surface and yield the treated particle. Preferably, the core particle has a density that is greater than the densities of the polymers of the inner layer and the outer layer (i.e., both the hydrophobic polymer and the catholyte). The core particle, for example, when it is porous, can be treated to be denser than the inner and outer layers. Thus, the density of the core particle can be inherent or as a result of treatment to render the particle of a certain density. Preferably, the density of the core particle is at least one and a half times greater than that of the polymers; more preferably, the density of the core particle is at least two times greater than that of the polymers.

As used herein, the term "catholyte" is the part of an electrolyte which is on the cathode side of an electrochemical cell that is effectively divided into two compartments. Catholyte is a by-product that is also produced onsite. Catholyte have an oxidation-reduction potential ("ORP") of about −800 to −900 mV. Catholyte is alkaline with a pH of about 10-13.

As used herein, the term "meta-stable substances" refers to isolated substances that spend an extended time in a configuration other than the substance's state of least energy. During a metastable state of finite lifetime all state-describing parameters reach and hold stationary values. The atoms of a substance in a metastable state can be excited but cannot emit radiation without a further supply of energy. The meta-stable substances of the present invention are formed by the attraction between the core particles and the layers. In order to remove the inner and outer layers, the energy level must be increased, for example by the application of heat to raise the thermodynamic energy level.

As used herein, the term "density" is synonymous with specific gravity and refers to the amount of matter that is in a certain volume. Density is measured as units of mass per units of volume.

As used herein, the term "sonication" refers to the act of applying sound energy to agitate particles in a sample, to form one or more coatings on the surface of a nano-particle. Ultrasonic frequencies (i.e., >20 kHz) are usually used, leading to the process also being known as ultrasonication or ultra-sonication.

As used herein, the term "sonochemical" refers to the process of treating particles in a sample with sound energy to promote a chemical reaction.

The method of coating the core particle can be any known process for applying coatings onto the surface of a core particle involving localized heat treatment. Preferably, the method used is based on sonochemical means employing for example, an Ultrasonic Processor, model # UPP-400A, Cycles: 20 KHz, available from Sonicor Instrument Corp., Copiague, N.Y. Typically, the particles are in a batch size of from about 100 grams to about 1 kilogram, and are sonicated to form the outer layer in a period of time of about 10 minutes to about 2 hours, and preferably 15 minutes to about 1 hour of sonication. The outer layer is formed in a way that it anchors the inner layer to the surface of the particle. During the time of sonication, the size of the particles increases as the coating of the two layers clad onto the surface of the particle. After sonicating, the particles are subjected to a centrifuge step whereby any residual anionic polymer is removed from the batch of treated particles. Finally after centrifuging, the particles are dried by placing them in an oven for about 12 to 19 hours at a temperature at least sufficient to remove by evaporation residual water, for example, about 100° C. to about 120° C.

The core particles may include any suitable materials, preferably, but not necessarily, materials capable of being formed into nano-sized particles. For example, the core particles may contain mineral pigments and mineral fillers such as, for example, talc, kaolin, mica, bismuth oxychloride, chromium hydroxide, barium sulfate, polymethylmethacrylate (PMMA), boron nitride, nylon beads, silica, or silica beads; lakes such as aluminum lake or calcium lake; metal oxides such as black, yellow or blue iron oxide, chromium oxide, zinc oxide or titanium dioxide; polymeric or plastic powders such as BPD 500 (HDI/Trimethylol Hexyllactone Crosspolymer and silica, available from Kobo Products, Inc., South Plainfield, N.J.); physical and chemical sun filters; salts, such as for example, sodium chloride, magnesium chloride, magnesium sulfate and calcium sulfate, potassium chloride, hydrated sodium sulfate, and magnesium bromide; sugars such as, for example, sucrose, dextrose, fructose, levulose, glucose, lactose, maltose, and galactose; proteins, polysaccharides, and other like organic and inorganic powders and particles. Preferably, the core particle comprises a metal oxide, such as titanium dioxide or zinc oxide.

More preferably, the core particles are nano-sized, having a particle size of less than about 100 nm (commonly referred to as nanoparticles), or still more preferably about 1.5 to about 90 nm, or most preferably about 10 to about 50 nm. The core particles, can be in any shape such as, for example, irregular, spherical, cylindrical, and plates. However, preferably they are cylindrical, or irregular due to their crystal structure. The core particles comprise about 10 to about 99 percent by weight of the treated particle; and preferably, about 40 to 90 percent by weight of the treated particle.

The inner layer is entrapped between the surface of the particle and the outer layer. The ability to entrap the inner layer is due to the branched moieties of the hydrophobic polymer of the outer layer. In addition, the inner layer has a higher density than the outer layer but a lower density than the core particle and contributes to the entrapment of the inner layer. The densities of the inner layer and the outer layer may be close but a difference between the inner layer and the outer layer of at least 0.01 in density achieves the desired effect of placing the inner layer beneath the outer layer on the surface of the core particle. The layering effect of the inner layer and the outer layer is also due to the different surface tension values inherent to the inner layer and the outer layer. The difference in density between the inner layer and the outer layer is such that the layering process of the two layers causes the outer layer to form on top of and penetrate through the inner layer by virtue of the branched moieties of the outer layer. The hydrophobicity of the inner and outer layer materials will affect layering. For example, ZnO prefers hydrophilic as opposed to hydrophobic substances. During the process, hydrophilic substances have a high affinity to the core particle and form the internal layer followed by the hydrophobic layer that form the outer layer.

The inner layer is formed from a hydrophilic solution containing cationic charges that can minimize free radical generation. The hydrophilic solutions have a positive charge with an electrical potential between 0.1 mV-120 mV, preferably between 5 mV-90 mV and more preferably between 24 mV-64 mV. The hydrophilic solutions are preferably catholyte solutions that are attracted to the core particle. The catholyte solutions can be formed from one or more salts, either natural or synthetic, with the required electrical potential. Any salts or a combination of two or more salts formed from positive ions (i.e., most of group 1 and 2 elements such as Na, Mg, Ca, etc.) that can combine with halogens (Cl, F, Br, etc) can be used. Some examples are NaCl, $CaCl_2$, $MgCl_2$, $CaBr_2$ and $TiCl_2$. In a preferred embodiment, using the chloralkali process, sodium chloride (NaCl), calcium chloride (CaCl) or aluminum chloride (AlCl) is electrolized to produce a catholyte solution with Na, Ca or Al ions present. Similar processes can be used with calcium bromide (CaBr) and calcium fluoride (CaF) to produce catholytes with Ca ions. When NaCl is used, the Na ions are attracted to and encapsulate the core particle, such as ZnO, since they have a high affinity for the free radicals generated by the core particle. In addition to a catholyte solution, other examples of suitable hydrophilic compositions include, but are not limited to, glycols, glycerin, water-based gums, carbomer gels, water-based gels, acrylates copolymers, methyl vinyl ether and maleic anhydride copolymers (PVM/MA, copolymers), and quaternary amine compounds. The cationic charge is capable of being dissolved in water and reacts with water to become water-soluble. The inner layer is present in an amount of about 0.2 to 5.0 percent by weight of the treated particle, and preferably, 0.5 to 2.0 percent by weight of the treated particle.

The inner layer can contain an active agent. As used herein, an active agent is defined as any material that possesses hydrophilic properties with positive charge. In a preferred embodiment, the inner layer further comprises the active agent, which is more preferably a hydrophilic active agent with a density similar to that of the inner layer. Examples of hydrophilic active agents include, but are not limited to, water-soluble preservatives, carbohydrates, water-soluble vitamins, amino acids, antioxidants, and synthetic and natural water-soluble extracts. The hydrophilic active agent can be present in the treated particle of the present invention in an amount of about 0.01 to 50.0 percent, preferably about 0.25 to 30.0 percent and most preferably about 0.50 to 10 percent by weight of the treated particle.

The outer layer of the treated particle is formed from a composition that includes a hydrophobic polymer, selected from, but not limited to: silicones that have dangling branched reactive alkoxyl moieties that penetrate through the inner layer to the core particle. While not wishing to be bound by any particular theory, it is believed that when the core particle is formed (e.g., by a metal oxide material), the branched reactive alkoxyl moieties extend from the outer layer through the inner layer onto the surface of the coated particle to form a covalent bond with the particle, thereby welding or anchoring the inner layer onto the coated particle. The hydrophobic polymers having the branched reactive alkoxyl moieties are based on silicones that include, but are not limited to: non-volatile silicones, such as dimethicone, dimethiconol, phenyl trimethicone, methicone, simethicone; resins such as siloxane resins and acrylate resins (polymerized synthetic thermosetting materials), polymers such as film-forming silicone polymers such as dimethicone copolyol, trimethylsiloxysilicate, and polymers having a fluorinated carbon chain, and can include oxazoline-modified organopolysiloxanes, vinyl copolymers (polymers consisting of two or more different monomers) containing a polysiloxane macromer, organopolysiloxanes having a sugar residue, alkyl-modified organopolysiloxanes, high polymerization organopolysiloxanes, oxazoline-modified organopolysiloxanes, homopolymers of a fluorine-containing vinyl monomer, copolymers containing a fluorine-containing vinyl monomer as a constituent and vinylidene fluoride-hexafluoroacetone copolymer, fluoroalkyl (meth)acrylates, fluoroalkyl (meth)acrylic amide esters, fluoroalkyl vinyl ethers and fluoro-α-olefins, of which (meth)acrylates having a fluoroalkyl group (having 6 to 12 carbon atoms). The outer layer is present in an amount of about 0.01 to about 50 percent of the treated particle, preferably about 0.5 to about 15 percent and most preferably about 1 to 10 percent of the treated particle.

In a preferred embodiment, the polymer has a silicone backbone with ethoxy or ethoxysilylethyl branched moieties. More preferably, the branched moieties in addition to ethoxy or ethoxysilylethyl comprise alkyl groups. Most preferably, the polymer is a reactive ethoxy modified silicone (as described in U.S. Pat. No. 6,660,281, which is incorporated herein by reference) that is available under the tradenames KF9901, KF9908, KF9909 or KP574 from ShinEtsu Silicones of America, Inc., Akron, Ohio. The reactive ethoxy modified silicone is also referred to as an ethoxysilylethyl (OEt) type silicone. For example, the ethoxysilylethyl type silicone can be a triethoxysilylethyl polydimethylsiloxyethyl hexyl dimethicone, which is commercially available under the name KF9909 from ShinEtsu Silicones of America, Inc., Akron, Ohio.

Figure 1:
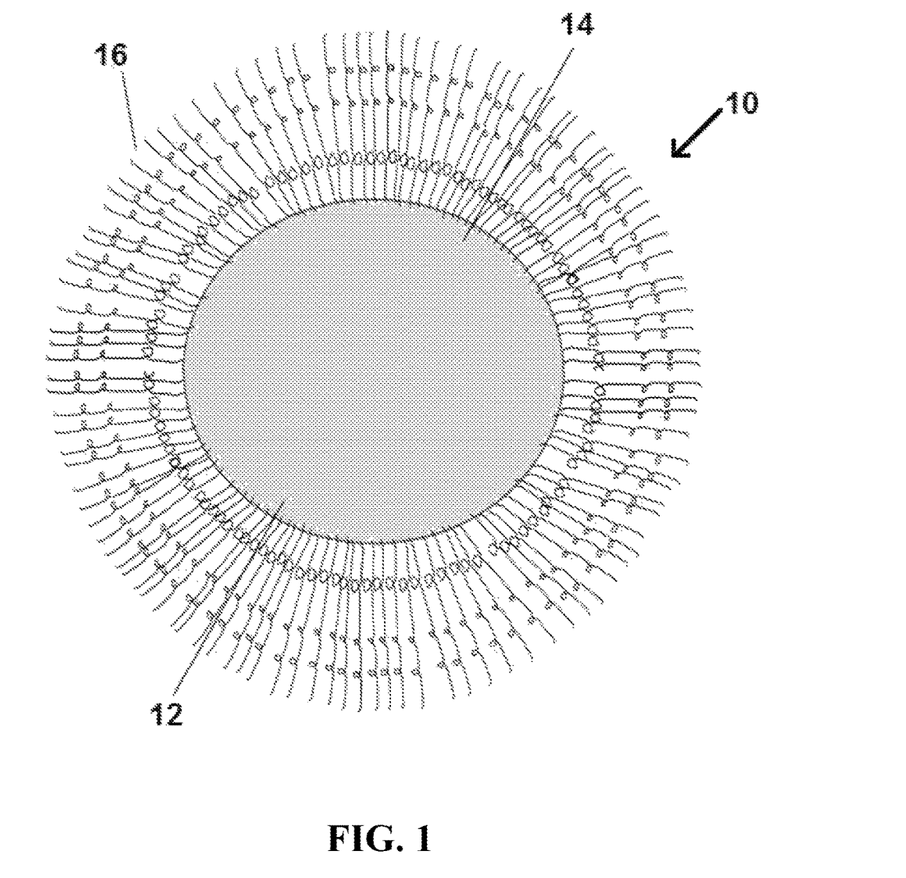
FIG. 1 is a cross-sectional view of an exemplary treated particle containing a core particle that is coated by an inner layer of a catholyte and an outer layer of a hydrophobic polymer, according to one embodiment of the present invention.

FIG. 1 is a cross-sectional view of an exemplary treated particle 10, according to one embodiment of the present invention. Specifically, a zinc oxide core particle 12 is coated by an inner layer 14 of a catholyte and an outer layer 16 of triethoxysilylethyl polydimethylsiloxyethyl dimethicone. The branched ethoxysilylethyl moieties of the triethoxysilylethyl polydimethylsiloxyethyl dimethicone extend from the outer layer through the inner layer to form a covalent bond with the zinc oxide on the surface of the core particle, thereby anchoring the catholyte contained by the inner layer onto the surface of the core particle. In this manner, the positive charge carried by the catholyte is localized or immobilized around the core particle. Optionally, the inner layer may further comprise a hydrophilic active agent (not shown), such as a cationic polymer.

The treated particles of the present invention, as illustrated hereinabove, can be readily formed, for example, by adding a catholyte solution and optionally a hydrophilic active agent, such as a cationic polymer, into water to solubilize the cationic polymer and the hydrophilic active agent. Core particles to be treated are then added into the aqueous solution of cationic charge materials and hydrophilic active agent and mixed until uniform. Subsequently, a hydrophobic polymer with branched reactive alkoxyl moieties is added into the aqueous solution, preferably with additional water. The mixture is sonicated for a sufficient period of time so as to form coated particles having an inner layer of anionic polymer and optional hydrophilic active agent and an outer layer of hydrophobic polymer, while the branched reactive alkoxyl moieties of the hydrophobic polymer extend from the outer surface through the inner surface onto the surface of the core particles.

The fully coated particles of the present invention can be added directly to any type of topical composition or formulation. The treated particles of the present invention prepared as described above is ready to be added to a cosmetically acceptable carrier or base of choice to form a topical composition. For purpose of the present invention, cosmetically acceptable carriers are substances that can be used to formulate the above-described active ingredients into a cream, gel, emulsion, liquid, suspension, nail coating, skin oil, or lotion that can be topically applied. Substances which may be formulated into the topical composition of the present application include, but are not limited to: moisturizing agents, astringent agents, chelating agents, surfactants, emollients, preservatives, stabilizers, thickeners, humectants, pigments, etc. Preferably, but not necessarily, such vehicles aid the formation of a protective layer on the skin. The vehicle or vehicles can present in the topical composition of the present invention at an amount ranging from about 1% to about 99.9%, preferably from about 50% to about 99.5%, more preferably from about 70% to about 99%, and most preferably from about 80% to 90% by total weight of the topical composition.

Such topical composition may contain one or more skin care additives, such as sunscreen agents, anti-aging agents, anti-acne agents, enzyme-inhibiting agents, collagen-stimulating agents, antioxidants, exfoliants, agents for the eradication of age spots, keratoses and wrinkles, analgesics, anesthetics, antibacterials, antiyeast agents, antifungal agents, antiviral agents, antidandruff agents, antidermatitis agents, antipruritic agents, antiemetics, anti-inflammatory agents, antihyperkeratolytic agents, antiperspirants, antipsoriatic agents, antiseborrheic agents, antiwrinkle agents, antihistamine agents, skin lightening agents, depigmenting agents, vitamins, corticosteroids, self-tanning agents, hormones, retinoids such as retinoic acid and retinol, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, topical steroids such as hydrocortisone, hydrocortisone 21-acetate, hydrocortisone I 7-valerate, and hydrocortisone I7-butyrate, betamethasone valerate, betamethasone diproprionate, benzoyl peroxide, crotamiton, propranolol, promethazine, vitamin A palmitate, vitamin E acetate and mixtures thereof.

The treated particles of the present invention provide various advantages and benefits that are not available in their untreated or "naked" counterparts. For example, the catholyte contained by the inner layer of the treated particles maintains the treated particles on the surface of the skin, so that such treated particles are less likely to settle into the wrinkles or creases on the skin surface. More importantly, when the core particle contains zinc oxide particles, which are known for releasing free reactive oxygen species upon UV exposure, the dual-layered coating of catholyte and the hydrophobic polymer can effectively neutralize or scavenge the released free oxygen radicals, and thereby reduce or eliminate any potential adverse impact that such free oxygen radicals may have on the surrounding environment. Consequently, the treated zinc oxide particles of the present invention can be readily incorporated into cosmetic compositions that contain skin care additives susceptible to oxidation by the free oxygen radicals, such as certain organic sunscreen agents (e.g., butyl methoxydibenzoylmethane) and organic dyes/colorants. Further, any potentially harmful effect that such free oxygen radicals may have on the human skin (which contains various biological components that are susceptible to oxidative attacks) can be effectively reduced or eliminated.

EXAMPLES

Example 1

Formation of Treated Zinc Dioxide Nanoparticles

To form treated zinc oxide nanoparticles according to the present invention, a catholyte and an optional cationic polymer were first added into a catholyte solution at the weight percentages specified in Formula I (Inner Layer Material) to solubilize the cationic polymer. The mixture formulated according to Formula I was then added into water together with nano-sized zinc oxide particles having an average particle size of about 35-45 nm at the weight percentages specified in Formula II and mixed until uniform to form nano-sized zinc oxide particles that are fully coated by cationic solution. Next, a hydrophobic polymer (triethoxysilylethyl polydimethylsiloxyethyl hexyl dimethicone) is added into the mixture of Formula II (i.e., the core particle coated with the inner layer material) at weight percentages specified in Formula III and mixed until uniform. Sonication is then carried out with intensity dial reading #5 (UPP-400A, Sonicor, Sonicor Instrument Co., West Babylon, N.Y.) for thirty minutes. The resulting mixture is placed in a centrifuge for about 15 minutes and subsequently washed with a volume of water at a 50:50 water-to-mixture ratio to remove residual cationic solution and hydrophobic polymer. Next, the centrifuged/washed mixture is placed in an oven at 105° C. for 19 hours to evaporate all of the water to form a powder, which is then ground to form fine treated zinc dioxide nanoparticles of the present invention.

Formula I: Inner Layer Material

| Ingredient | Weight % |
| --- | --- |
| Catholyte | 97-99 |
| Optional cationic polymer | 1-3 |

Formula II: Core Particle Coated with the Inner Layer Material

| Ingredient | Weight % |
| --- | --- |
| Formula 1 | 80 |
| Nanosized zinc oxide | 20 |

Formula III: Treated Particles

| Ingredient | Weight % |
| --- | --- |
| Formula 2 | 95.24 |
| triethoxysilylethyl polydimethylsiloxyethyl hexyl dimethicone | 4.76 |

Figure 2A:
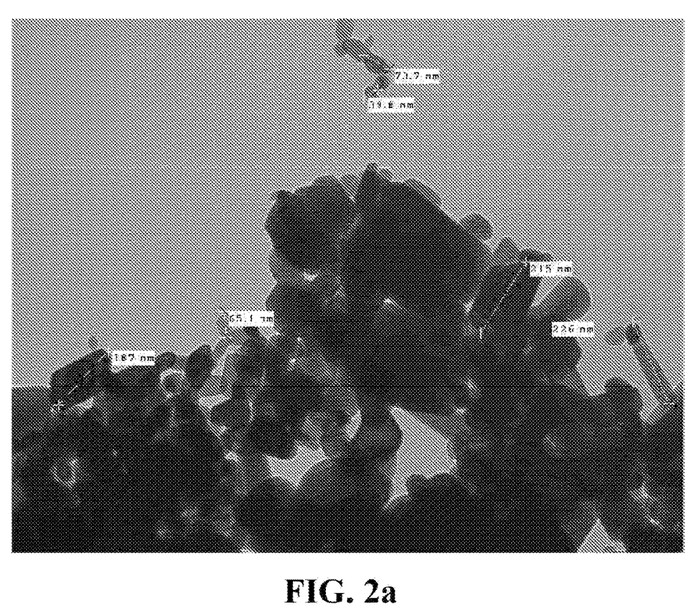
FIGS. 2a and b are Transmission electron microscopic ("TEM") images of zinc oxide nanoparticles coated with an inner layer of a catholyte and an outer layer of a triethoxysilylethyl polydimethylsiloxyethyl hexyl dimethicone, according to one embodiment of the present invention.
Figure 2B:
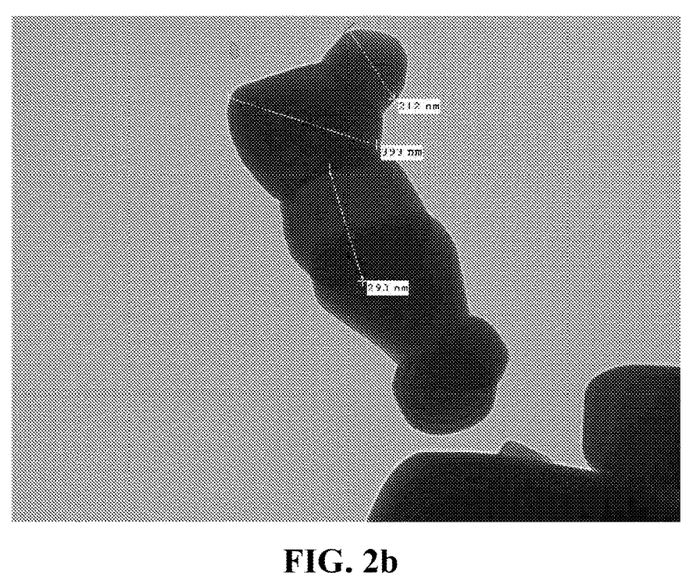

FIGS. 2a,b show transmission electron microscopic ("TEM") images of the treated zinc dioxide nanoparticles and untreated nanoparticles formed according to the method described hereinabove. The average particle size of such treated zinc oxide nanoparticles is about 45 nm.

Example 2

Impact of the Treated Zinc Oxide Nanoparticles on Cell Growth

The impact of the treated zinc oxide particles of the present invention on cell growth was measured. Cells used in the study were dermal fibroblasts of a 31 year old Caucasian female (CF-31).

First, a set of the dermal fibroblast cells were cultured in polystyrene Petri dishes (the culture dish) containing a mixed cell culture solution, which consisted of cell growth medium (Dulbecco's Modified Eagle Medium, high glucose with L-glutamine pyridoxine HCl without sodium pyruvate, GIBCO) and 10% Fetal Bovine Serum (Invitrogen Corporation, presently, Grand Island Biological Co. (GIBCO)) (hereinafter referred to collectively as media/serum).

The media provided cells with essential nutrients such as amino acids, sugars and ions that were needed for maintaining the physiological environment of the cells. In addition, the glucose in the media acted as an energy source for the dividing cells. The serum contained proteins that are incorporated into the ECM (extracellular matrix). Mather, J. P., Barnes, D., Methods in Cell Biology, Vol. 57, Academic Press, London, 20-21, 25 (2002). Once the cells reached approximately 10-13 passages, indicating that they were confluent, the cells were plated for experimentation. The media/serum was removed from the culture dish and rinsed twice with Dulbecco's Phosphate Buffered Saline (PBS, Invitrogen Corporation, GIBCO). Because the cells were stuck to the culture dish, Trypsin-EDTA (GIBCO), a protease, was added to enzymatically digest the cell membrane and detach the cells from the surface. After 5 minutes of incubation (at 37.4 C, 5% $CO_2$, with humidity generated by a volume of water in a range sufficient to fill a Petri dish to sufficient to fill a 50 ml beaker (i.e., about 10 to 50 ml)), media was added to stop the reaction. The number of cells per milliliter of solution was calculated by using hemocytometer to determine what amount should be added per well to generate a density of 2,000 cells per well in a 24-well dish. After the number of cells was calculated, they were plated on sterile glass cover slips, and 1 milliliter of media solution was added to each well. One of the media solutions added was a control solution that contained no treated zinc oxide nanoparticles. Other two media solutions added were sample solutions that contained treated zinc oxide nanoparticles at respective concentrations of about 0.05 mg/ml. After the cells were plated, they were incubated for 24 hours, so that the cells could attach to the cover slip and adjust to the new conditions.

The cell growth patterns were then evaluated for a period of 1 to 11 days by counting the average number of cells in each well, while the cells were exposed to different media solutions (i.e., the control solution and the sample solution) containing treated zinc oxide nanoparticles at 0.05 mg/ml concentrations. First, the media solution was removed from the wells, and the samples were rinsed twice with PBS. Trypsin-EDTA was added to each well, and the samples were incubated for about 5 minutes to completely cleave the cells from the surface. The cell-Trypsin solutions in each well were added and combined in a single test tube, and media was added to stop the trypsin reaction. The solutions in the test tube were centrifuged, and the supernatant liquid was removed from the test tube such that only the cell pellet remained at the bottom of the test tube. The cells were re-suspended in media, and 10 microliters of the solution was placed in each side of a hemacytometer to be counted.

The solution was placed under an optical microscope and counted in a grid having four corners and a center box that appeared on each side of the hemacytometer. The cells in the four corners and center box were counted. The number of cells per well was calculated using the following formula:

($N$×10 4×)$X$=cells per well, where N is the number of cells counted, V is the total volume of X, and X is the number of wells counted.

Figure 3:
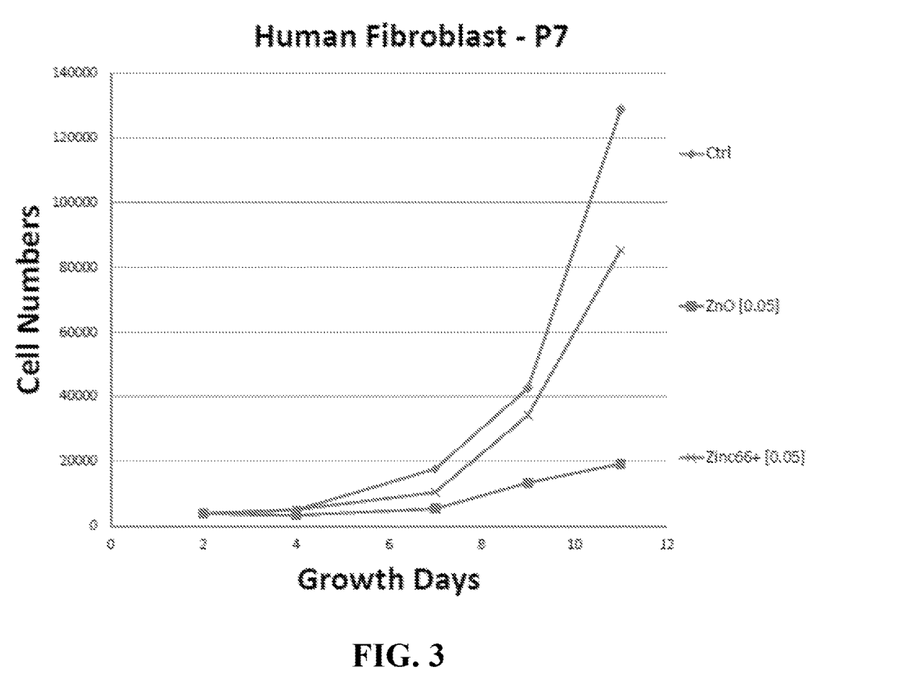
FIG. 3 shows the growth curves of skin dermal fibroblast cells that were in contact with coated zinc oxide nanoparticles of the present invention at different concentrations.

Growth curves of dermal fibroblast cells were constructed for cells grown in media solutions containing treated zinc oxide nanoparticles at 0.05 mg/ml concentrations, by plotting the average number of cells per well observed as a function of time. The resulting growth curves were shown in FIG. 3. Specifically, the growth curves of dermal fibroblast cells grown in the sample solution containing about 0.05 mg/ml of treated zinc oxide nanoparticles are substantially parallel to the growth curve of those cells grown in the control solution containing no treated zinc oxide nanoparticles, which indicates that the treated zinc oxide nanoparticles of the present invention have little or no adverse impact on the growth of the dermal fibroblast cells.

Example 3

Effectiveness of Treated and Untreated Zinc Oxide Nanoparticles in Protecting λ DNA Molecules Against UV Damages Photodegradation tests were further carried out using k-phase DNA molecules to evaluate the overall effectiveness of the treated and untreated zinc oxide nanoparticles in protecting λ DNA against UV damages. Specifically, a solution of λ DNA (48,502 base pairs) in 1×TE buffers at a concentration of about 50 μg/ml was prepared, and into which 2 mg/ml of either untreated or "naked" zinc oxide nanoparticles (rutile) or treated zinc oxide nanoparticles of the present invention was added. Each sample solution was placed under different UV sources, including sources for UVA at 350 nm, UVB at 300 nm, and UVC at 253 nm (available from UVP, Inc. at Upland, Calif.). The exposure times varied from 1 to 6 hours, depending on the types of UV lights. Gel electrophesis of the λ DNA molecules under different UV light exposure conditions and with or without contact with naked or treated zinc oxide nanoparticles was then prepared using 0.8% (w/v) agarose in 1×TAE buffer, while an electric field of 5V/cm was applied to the gel for 30 minutes. The gel electrophoresis results are shown in FIGS. 4a-c.

Figure 4A:
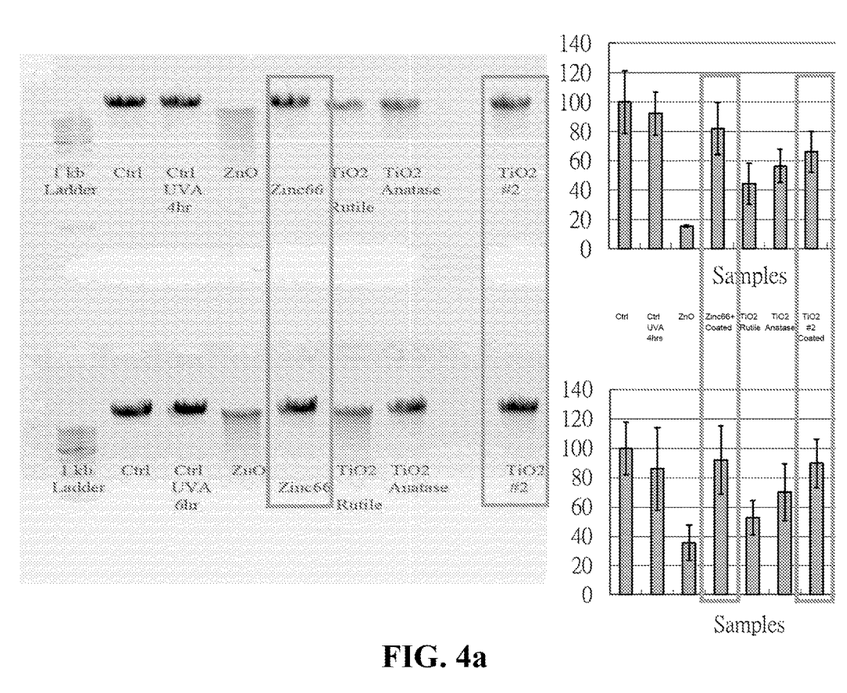
FIGS. 4a and 4b show the agarose gel electrophoresis pictures of deoxyribonucleic acid (DNA) molecules from enterobacteria phage λ. (hereinafter "λDNA molecules"), while the λ DNA molecules were placed under different ultraviolet ("UV") light exposure conditions, i.e., long wave (extends from about 320 to 400 nm in wavelength) UV ("UVA") and short wave (extends from about 200 to 280 nm in wavelength) UV ("UVC").

In FIG. 4a, the first and leftmost column is a control column consisting of a 1 Kbp ladder, which functions as a molecular weight marker for DNA fragments of different sizes. Column 2 corresponds to λ DNA that was not exposed to any UV light and therefore undamaged or unfragmented. Unfragmented λ DNA was too large to elute through the gel channel and therefore all remained at the input end of the gel channel. Column 3 corresponds to λ DNA that was exposed to UVA for 4 hours top and 6 hours bottom, which shows little or no damage or fragmentation, indicating that the 4 hours and 6 hours of UVA exposure resulted in little or no DNA damage. Column 4 corresponds to λ DNA that was mixed with naked zinc oxide nanoparticles and exposed to UVA for 4 hours top and 6 hours bottom, which shows significant reduction in intensity of the DNA at the input end of the gel channel for both 4 hours and 6 hours. This indicates that the λ DNA in contact with the naked zinc oxide particles was significantly fragmented, and the resulting DNA fragments were eluted rapidly into the gel channel. Column 5 corresponds to λ DNA that was mixed with treated zinc oxide nanoparticles of the present invention and exposed to UVA for 4 hours top and 6 hours bottom, which shows little or no reduction in the DNA intensity. This indicates that the λ DNA molecules in contact with the treated zinc oxide nanoparticles of the present invention was not significantly damaged or fragmented, unlike those in contact with the untreated or naked zinc oxide nanoparticles.

Figure 4B:
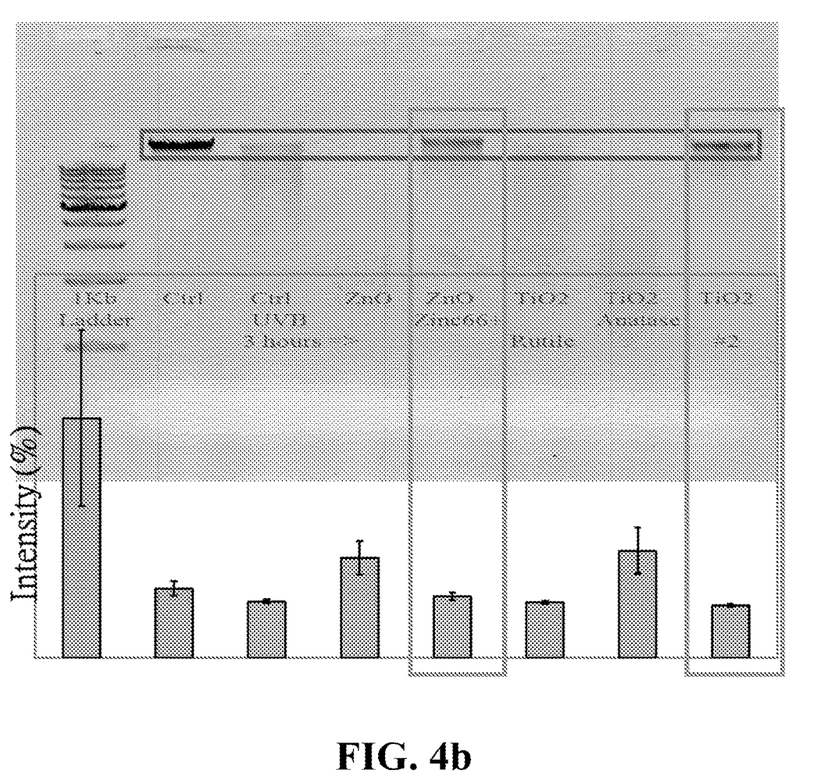

In FIG. 4b, column 3 corresponds to λ DNA that was exposed to UVB for 3 hours, which shows significant DNA fragmentation, indicating that the 3 hours of UVB exposure resulted in significant DNA damage. Column 4 corresponds to λ DNA that was mixed with naked zinc oxide nanoparticles and exposed to UVB for 3 hours, which shows near complete fragmentation and elution of the DNA molecules. Column 5 corresponds to λ DNA that was mixed with treated zinc oxide nanoparticles of the present invention and exposed to UVB for 3 hours, which shows significantly less DNA fragmentation than both Column 3 and 4. This indicates that the treated zinc oxide nanoparticles of the present invention were effective in protecting the DNA molecules against the UVB radiation, without imposing any additional damage thereupon.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

We claim:

1. A method for forming meta-stable substances comprising:
    preparing an aqueous hydrophilic catholyte solution having a positive charge with an electrical potential between 0.1 mV-120 mV and a first density, wherein the aqueous hydrophilic catholyte solution consists of water and metal halogen salts;
    adding one or more nano-sized core particles having a second density to the aqueous hydrophilic catholyte solution and mixing;
    adding a hydrophobic polymer having a third density to the core particles and aqueous solution and mixing to form a mixture;
    sonicating the mixture to form coated particles having an inner coating layer and an outer coating layer;
    separating the coated particles from the mixture; and
    drying the coated particles.

2. The method for forming meta-stable substances according to claim 1, wherein the nano-sized core particles are metal oxides.

3. The method for forming meta-stable substances according to claim 2, wherein the metal oxides are zinc oxides or titanium oxides.

4. The method for forming meta-stable substances according to claim 1, wherein the first density of the aqueous hydrophilic catholyte solution is greater than the third density of the hydrophobic polymer.

5. The method for forming meta-stable substances according to claim 1, wherein the second density of the core particles is greater than the first and second densities.

6. The method for forming meta-stable substances according to claim 1, wherein the hydrophobic polymer comprises a silicone having dangling branched reactive alkoxyl moieties.

7. The method for forming meta-stable substances according to claim 1, wherein the hydrophobic polymer comprises dimethicone, dimethiconol, phenyl trimethicone, methicone, simethicone, siloxane resins, acrylate resins, dimethicone copolyol, trimethylsiloxysilicate, polymers having a fluorinated carbon chain, oxazoline-modified organopolysiloxanes, vinyl copolymers (polymers consisting of two or more different monomers) containing a polysiloxane macromer, organopolysiloxanes having a sugar residue, alkyl-modified organopolysiloxanes, high polymerization organopolysiloxanes, oxazoline-modified organopolysiloxanes, homopolymers of a fluorine-containing vinyl monomer, copolymers containing a fluorine-containing vinyl monomer as a constituent and vinylidene fluoride-hexafluoroacetone copolymer, fluoroalkyl (meth)acrylates, fluoroalkyl (meth)acrylic amide esters, fluoroalkyl vinyl ethers, or (meth)acrylates having a fluoroalkyl group with 6 to 12 carbon atoms.

8. The method for forming meta-stable substances according to claim 1, wherein the nano-sized core particles comprise talc, kaolin, mica, bismuth oxychloride, chromium hydroxide, barium sulfate, polymethylmethacrylate (PMMA), boron nitride, nylon beads, silica, silica beads, aluminum lake, calcium lake, black, yellow or blue iron oxide, chromium oxide, zinc oxide, titanium dioxide, polymeric or plastic powders, sodium chloride, magnesium chloride, magnesium sulfate, calcium sulfate, potassium chloride, hydrated sodium sulfate, magnesium bromides, sucrose, dextrose, fructose, levulose, glucose, lactose, maltose, galactose, proteins or polysaccharides.

9. The method for forming meta-stable substances according to claim 1, wherein the mixture is sonicated for from 10 minutes to 2 hours.

10. The method for forming meta-stable substances according to claim 1, wherein the coated core particles are dried at a temperature of from about 100° C. to about 120° C.

11. The method for forming meta-stable substances according to claim 1, wherein the nano-sized core particles have a particle size of less than 100 nm.

12. The method for forming meta-stable substances according to claim 1, wherein the weight of the nano-sized core particles is about 40 to about 90 percent of the weight of the coated particles.

13. The method for forming meta-stable substances according to claim 1, wherein the weight of the inner layer is about 0.2 to 5.0 percent of the total weight of the coated particle.

14. The method for forming meta-stable substances according to claim 1, wherein the weight of the hydrophobic polymer is about 0.01 to about 50 percent of the total weight of the coated particle.

15. A method for forming meta-stable substances comprising:
preparing an aqueous catholyte solution consisting of water and one or more metal halogen salts and having a first density;
adding one or more nano-sized core particles having a second density to the aqueous catholyte solution and mixing;
adding a hydrophobic polymer having a third density to the core particles and aqueous solution and mixing to form a mixture;
sonicating the mixture to form coated particles having an inner coating layer and an outer coating layer;
separating the coated particles from the mixture; and
drying the coated particles.

16. The method for forming meta-stable substances according to claim 15, wherein the nano-sized core particles are metal oxides.

17. The method for forming meta-stable substances according to claim 15, wherein the hydrophobic polymer comprises a silicone having dangling branched reactive alkoxyl moieties.

18. The method for forming meta-stable substances according to claim 15, wherein the metals in the metal halogen salts of the aqueous catholyte solution are sodium (Na) ions, calcium (Ca) ions, magnesium (Mg) ions, titanium (Ti), aluminum (Al) ions or a combination of one or more thereof.

19. The method for forming meta-stable substances according to claim 15, wherein the mixture is sonicated for from 10 minutes to 2 hours and the coated core particles are dried at a temperature of from about 100° C. to about 120° C.

20. The method for forming meta-stable substances according to claim 15, wherein the nano-sized core particles have a particle size of less than 100 nm.

* * * * *